United States Patent
Xue et al.

(10) Patent No.: US 9,603,539 B2
(45) Date of Patent: Mar. 28, 2017

(54) SYSTEMS AND METHODS FOR MODELING ELECTRICAL ACTIVITY OF AN ANATOMICAL STRUCTURE

(75) Inventors: Joel Q. Xue, Germantown, WI (US); Weihua Gao, Shanghai (CN); Yao Chen, Shanghai (CN); Xiaodong Han, Shanghai (CN)

(73) Assignee: General Electric Company, Schenectady, NY (US)

( * ) Notice: Subject to any disclaimer, the term of this patent is extended or adjusted under 35 U.S.C. 154(b) by 156 days.

(21) Appl. No.: 13/255,136

(22) PCT Filed: Apr. 20, 2009

(86) PCT No.: PCT/CN2009/000416
§ 371 (c)(1),
(2), (4) Date: Sep. 7, 2011

(87) PCT Pub. No.: WO2010/121390
PCT Pub. Date: Oct. 28, 2010

(65) Prior Publication Data
US 2012/0030255 A1    Feb. 2, 2012

(51) Int. Cl.
*G06F 19/00*    (2011.01)
*A61B 5/0468*    (2006.01)
(Continued)

(52) U.S. Cl.
CPC .......... *A61B 5/04012* (2013.01); *A61B 5/044* (2013.01); *G06F 19/3437* (2013.01)

(58) Field of Classification Search
None
See application file for complete search history.

(56) References Cited

U.S. PATENT DOCUMENTS

| 5,634,469 A * | 6/1997 | Bruder et al. ........... 600/512 |
| 6,920,350 B2 * | 7/2005 | Xue et al. ............... 600/523 |

(Continued)

FOREIGN PATENT DOCUMENTS

| WO | 2005072607 A1 | 8/2005 |
| WO | 2007035306 A2 | 3/2007 |

OTHER PUBLICATIONS

Chinese International Search Report dated Dec. 31, 2009 for PCT Application No. PCT/CN2009/000416 which was filed on Apr. 20, 2009.

(Continued)

*Primary Examiner* — Lori A Clow
(74) *Attorney, Agent, or Firm* — GE Global Patent Operation; Marc A. Vivenzio

(57) ABSTRACT

A system for modeling electrical activity of an anatomical structure. The system includes a database that is configured to store cell set data corresponding to a group of cells of the anatomical structure. The cell set data includes a cell model that represents electrical activity of the group of cells. The cell model has a model parameter that relates to ion channels in the cells. The electrical activity represented by the cell model is at least partially based upon the model parameter. The system also includes a user interface that is configured to accept user inputs to change the model parameter and thereby change the electrical activity represented by the cell model to form a reconfigured cell model. The system also includes a display that is configured to display the user inputs and a processor that is configured to determine the electrical activity of the anatomical structure using the reconfigured cell model.

15 Claims, 10 Drawing Sheets

(51) Int. Cl.
*A61B 5/00* (2006.01)
*A61B 5/04* (2006.01)
*A61H 31/00* (2006.01)
*A61B 5/044* (2006.01)

(56) References Cited

U.S. PATENT DOCUMENTS

| | | | |
|---|---|---|---|
| 7,142,907 B2* | 11/2006 | Xue et al. | 600/509 |
| 7,593,764 B2* | 9/2009 | Kohls et al. | 600/509 |
| 7,769,434 B2* | 8/2010 | Xue | 600/509 |
| 2006/0149217 A1 | 7/2006 | Hartlep et al. | |
| 2008/0082013 A1 | 4/2008 | Xue et al. | |
| 2008/0154143 A1 | 6/2008 | Xue et al. | |
| 2008/0177192 A1 | 7/2008 | Chen et al. | |
| 2008/0312522 A1 | 12/2008 | Rowlandson et al. | |

OTHER PUBLICATIONS

Gao et al., "Using a Cell-to-ECG Model to Evaluate Ischemia Detection from Different Lead Sets", Computers in Cardiology, vol. No. 34, pp. 329-332, 2007.

Xue, Joel et al., "Study of Repolarization Heterogeneity and Electrocardiographic Morphology with a Modeling Approach", Journal of Electrocardiology, vol. No. 41, pp. 581-587, 2008.

UK Office Action issued in connection with corresponding GB Application No. GB1117968.6 on Jan. 17, 2014.

Shimizu et al., "Sodium Pentobarbital Reduces Transmural Dispersion of Repolarization and Prevents Torsades de Pointes in Models of Acquired and Congenital Long QT Syndrome", Journal of Cardiovasc Electrophysiology, vol. 10, No. 2, pp. 154-164, Feb. 1999.

Antzelevitch et al., "Electrophysiological Effects of Ranolazine, a Novel Antianginal Agent With Antiarrhythmic Properties", Circulation, vol. 110, No. 8, pp. 904-910, Aug. 2004.

* cited by examiner

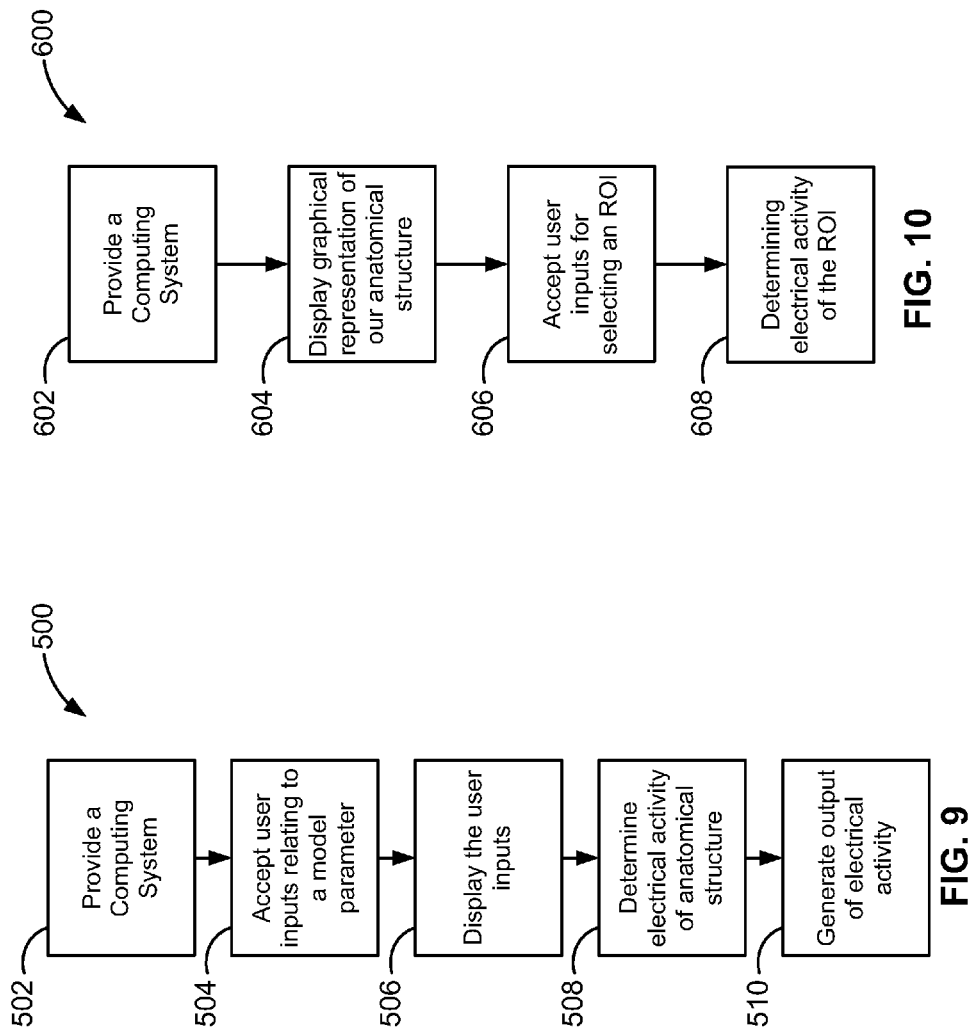

SYSTEMS AND METHODS FOR MODELING ELECTRICAL ACTIVITY OF AN ANATOMICAL STRUCTURE

BACKGROUND OF THE INVENTION

The subject matter herein relates generally to systems and methods for modeling electrical activity of an anatomical structure, and more particularly, to systems and methods for modeling cardiac electrical activity.

Electrocardiographic (ECG) data represents the combined electrical activity of the cells of the heart, also referred to as cardiac cells. The cardiac cells experience electrical impulses called action potentials that cause the cardiac cells to contract after stimulation. The cardiac cells in different regions and layers (i.e., cardiac cells having different spatial positions in the heart) may experience different types of action potentials at different times during a cardiac cycle. The combined electrical activity of the cardiac cells during the cardiac cycle may be detected as a waveform showing electrical potential over time. For example, one conventional method of collecting ECG data uses ten electrodes that are placed on the skin of a patient in predetermined locations. Each cardiac cycle may be recorded as a PQRST waveform or complex, where the letters P, Q, R, S, and T represent different waves or deflections in the PQRST waveform. Generally, a P-wave corresponds to activity in the atria, a QRS complex represents the electrical activation of the ventricles, and a T-wave represents electrical recovery or a recharge phase of the ventricles.

The PQRST waveform may be analyzed to identify waveform features (e.g., QT interval, shape of T-wave, ST segment, T peak to T end (TpTe) interval) that may be associated with cardiac conditions. For example, a prolonged QT interval has been associated with potentially life threatening medical conditions, such as cardiac arrhythmia. As such, if a pharmaceutical company discovers that a drug under study may cause a prolonged QT interval, the company may cease its research of that drug. However, the QT interval has several limitations. First, the QT interval may not be highly correlative with some severe medical conditions. For example, a drug may affect the electrical activity of cardiac cells in certain regions of the heart such that the electrical activity of the cardiac cycle is ultimately recorded by an ECG monitor as having a prolonged QT interval. However, the affected cardiac cells may not represent a threat to the health of the patient. As such, viable and potentially helpful drugs may be excluded from further study due to erroneous concerns over the drug's safety. Second, the QT interval is dependent upon the heart rate and, consequently, the QT interval is usually corrected before analysis, which introduces another level of error. Also, the QT interval can be difficult to measure and analyze.

Accordingly, researchers and health practitioners are seeking alternative waveform features that may better identify cardiac conditions of interest. However, some current methods of identifying such waveform features include obtaining ECG data from patients and, after diagnosing a cardiac condition of the patients or recording a final event (e.g., heart attack), determining if any waveform features are associated with the cardiac condition or the final event. Such methods may be expensive and time-consuming. Other methods include using cell or tissue models that simulate the electrical activity of the cardiac cells. However, these methods may not model the whole heart, and may not determine the ultimate waveforms that may be detected through, for example, the conventional twelve lead ECG and/or do not provide a user-friendly format for analyzing and investigating waveform features.

Also, another problem faced by researchers and health practitioners may be the PQRST waveform itself. Although useful in identifying and determining some cardiac conditions, the current standard arrangement of ten electrodes provides only one view of the electrical activity of the heart. Many other arrangements of electrodes may be used to provide more easily identifiable waveform features that are associated with cardiac conditions. However, the cost in finding such waveform features may be prohibitive.

Accordingly, there is a need for systems and methods that identify waveform features associated with health conditions of interest. There is also a need for systems and methods that determine arrangements of electrodes that may facilitate detecting such waveform features. Furthermore, there is a need for user-friendly systems and methods for modeling electrical activity of an anatomical structure

BRIEF DESCRIPTION OF THE INVENTION

In one embodiment, a system for modeling electrical activity of an anatomical structure is provided. The system includes a database that is configured to store cell set data corresponding to a group of cells of the anatomical structure. The cell set data includes a cell model that represents electrical activity of the group of cells. The cell model has a model parameter that relates to ion channels in the cells. The electrical activity represented by the cell model is at least partially based upon the model parameter. The system also includes a user interface that is configured to accept user inputs to change the model parameter and thereby change the electrical activity represented by the cell model to form a reconfigured cell model. The system also includes a display that is configured to display the user inputs and a processor that is configured to determine the electrical activity of the anatomical structure using the cell model including the reconfigured cell model.

In another embodiment, a method for modeling electrical activity of an anatomical structure is provided. The method uses a computing system that includes a database configured to store cell set data that represents a group of cells of the anatomical structure. The cell set data includes a cell model that represents electrical activity of the group of cells. The cell model has a model parameter of ion channels in the cells. The electrical activity represented by the cell model is at least partially based upon the model parameter. The method includes accepting user inputs that relate to the model parameter. The user inputs change the electrical activity represented by the cell model to form a reconfigurable cell model. The method also includes displaying the user inputs and determining the electrical activity of the anatomical structure using the reconfigurable cell model.

In yet another embodiment, a system for modeling electrical activity of an anatomical structure is provided. The system includes a database that is configured to store cell set data that represents a group of cells of the anatomical structure. The cell set data includes a cell model that represents electrical activity of the group of cells. The system also includes a display that is configured to display a graphical representation of the anatomical structure and a user interface. The user interface is configured to accept user inputs for selecting a region-of-interest (ROI) within the anatomical structure. The ROI includes the group of cells and is indicated on the graphical representation. The system also includes a processor that is configured to determine the electrical activity of the ROI based upon the cell model. The processor is configured to generate an output indicative of the electrical activity of the ROI.

In another embodiment, a method for modeling electrical activity of an anatomical structure is provided. The method uses a computing system that includes a database configured to store cell set data that represents a group of cells of the anatomical structure. The cell set data includes a cell model that represents electrical activity of the group of cells. The method includes displaying a graphical representation of the anatomical structure and accepting user inputs for selecting a region-of-interest (ROI) within the anatomical structure. The ROI includes the group of cells and is indicated on the graphical representation of the anatomical structure. The method also includes determining the electrical activity of the ROI based upon the cell model and generating an output indicative of the electrical activity of the ROI.

BRIEF DESCRIPTION OF THE DRAWINGS

FIG. 9 illustrates a method of modeling electrical activity of an anatomical structure formed in accordance with one embodiment.

FIG. 10 illustrates another method of modeling electrical activity of an anatomical structure formed in accordance with one embodiment.

DETAILED DESCRIPTION OF THE INVENTION

Figure 1:
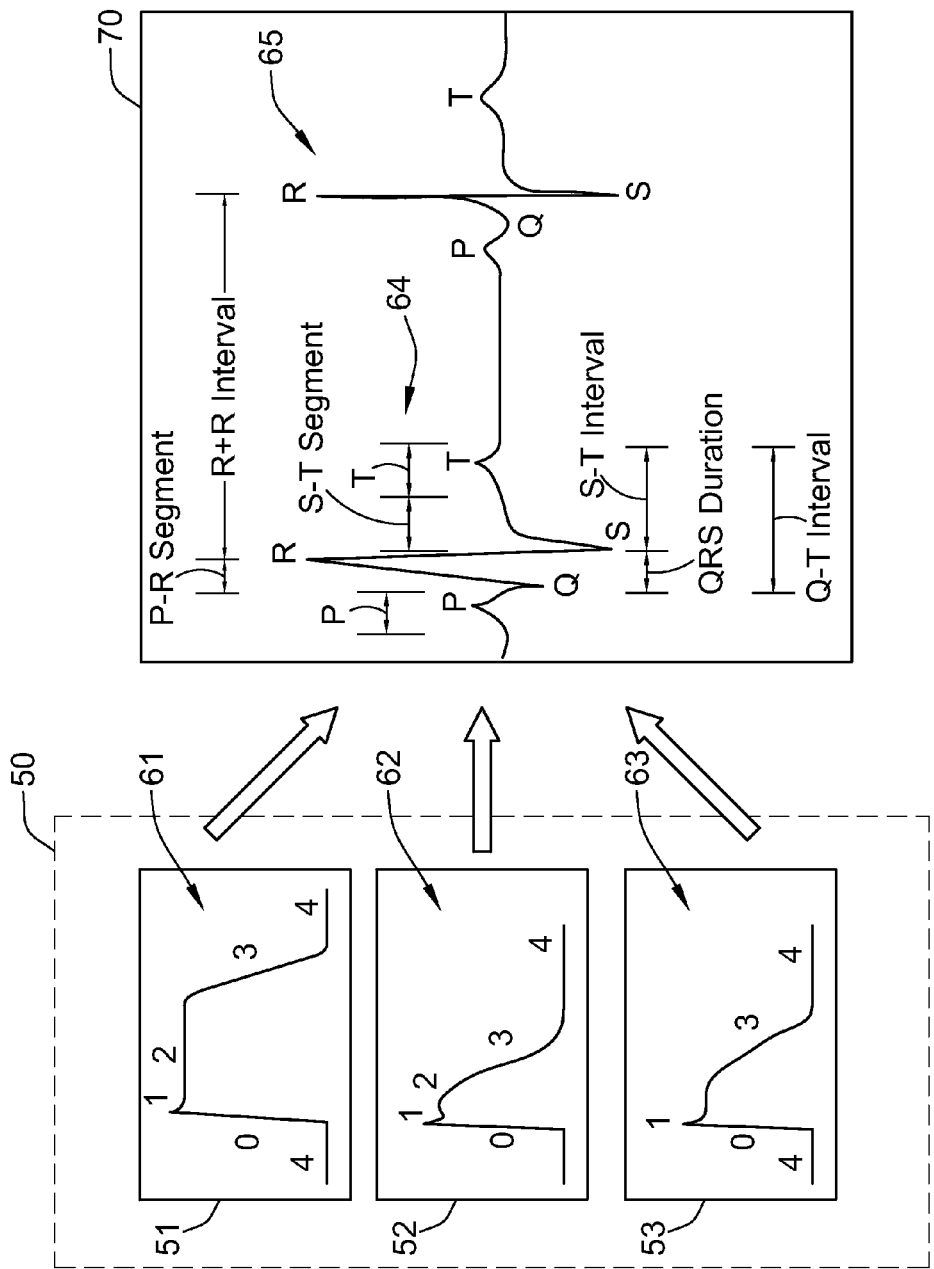
FIG. 1 is a block diagram illustrating electrical activity of cells and waveform data measured therefrom.

Exemplary embodiments that are described in detail below provide systems and methods that facilitate analyzing electrical activity of cells within an anatomical structure. In particular embodiments, the systems and methods provided herein may facilitate analyzing the electrical activity of cardiac cells and identifying waveform features that may be associated with cardiac conditions of interest. In some embodiments, the systems and methods may facilitate determining a number and arrangement of electrodes on a surface of a body of a patient in order to measure desired waveforms. Also, some embodiments may provide a system that is user-friendly. For example, some embodiments may be capable of demonstrating simultaneous or synchronized activity of different features of the heart during a cardiac cycle.

It should be noted that although the various embodiments may be described in connection with electrical functioning of the heart, the methods and systems described herein are not limited to cardiac electrophysiology. As such, an "anatomical structure," as used herein, includes the heart or heart structures therein, as well as other organs, brain, skeletal muscular structures/system, lung, and nerve structures/system. However, embodiments may also be used to analyze blood flow within the heart and body. Data provided or determined by the systems and methods described herein may relate to a human or an animal. As such, a "patient," as used herein, may be a human or animal. Also, an anatomical structure may be an entire organ or system or may be an identifiable region or structure within the organ or system. Examples of anatomical structures of the heart include, but are not limited to, one or both ventricles, one or both atria, epicardium, endocardium, mid-myocardium, the sinoatrial (SA) node, a group of cardiac cells within a predetermined region of the heart, and conductive pathways of the heart. Anatomical structures may also be the entire skeletal muscle system or predetermined muscle(s) and the nervous system or identifiable nerves within the nervous system.

Furthermore, U.S. Patent Application Publication Nos. 2008/0177192; 2008/0132799; 2008/0082013; 2008/0154143; and 2008/0312522 include subject matter similar to the subject matter described herein and are all incorporated by reference in their entirety. Also, articles by Xue et al., "Study of Repolarization Heterogeneity and Electrocardiographic Morphology with a Modeling Approach," Journal of Electrocardiology, 41 (2008) 581-587, and by Gao et al., "Using a Cell-to-ECG Model to Evaluate Ischemia Detection from Different Lead Sets," Computers in Cardiology, (2007) 34:329-332, also include subject matter similar to the subject matter described herein and are both incorporated by reference in their entirety.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 is a block diagram illustrating waveform data 70 that represents the detected electrical activity of an anatomical structure 50. Cell-based windows 51-53 are shown for exemplary biological cells that may be found within the anatomical structure 50. The anatomical structure 50 may include several thousands or millions of biological cells. In the illustrated embodiment, the biological cells represented by the cell-based windows 51-53 are cardiac cells, however the biological cells may also be nerve cells, muscle cells, and the like. Cardiac cells generally experience action potentials, which are waves of electrochemical activity that propagate through the cardiac cells. Exemplary action potentials are represented by action potential (AP) waveforms 61-63 in the cell-based windows 51-53, respectively. The AP waveforms 61-63 reflect changes in membrane potential (mV) (vertical axis) of a corresponding cardiac cell over time (ms) (horizontal axis). The action potentials result from ion current changes with their own channels controlled by one or multiple gates, within a cardiac cell, that open and close during a cardiac cycle, thereby changing the membrane potential of the cardiac cell. As shown in the cell-based windows 51-53, the cardiac cells may transition through phases where the membrane potential changes, such as the phases denoted by reference numerals 0, 1, 2, 3, and 4 along the AP waveforms 61-63. However, other cardiac cells may have action potentials that show different AP waveforms.

Phase 4 corresponds to the resting membrane potential and occurs when the cell is not being stimulated. Once the cell is electrically stimulated (e.g., by an electric current from an adjacent cell), the cell begins a sequence of actions involving the influx and efflux of multiple cations and anions through the ion channels that together produce a corresponding action potential of the cell. The corresponding action potential propagates and electrically stimulates adjacent cell or cells. Phase 0 represents a rapid depolarization phase. The slope of phase 0 represents a maximum rate of depolarization of the cell and is typically caused by an influx of sodium ions through ion channels. Phase 1 occurs with the inactivation of sodium ion channels. Phase 2 represents a plateau phase and Phase 3 occurs during a rapid repolarization of the cardiac cell that returns the membrane potential to the resting membrane potential.

By way of example, the AP waveform 61 may represent an AP waveform of a cardiac cell in the epicardium, the AP waveform 62 may represent an AP waveform of a M cell in the midmyocardium, and the AP waveform 63 may represent an AP waveform of a cardiac cell in the endocardium. However, other cardiac cells within the anatomical structure 50 may have different AP waveforms due to several factors, including the number, type, or distribution of ion channels within the cardiac cell. Furthermore, the AP waveforms may change as a result of the ion channels being affected by drugs.

The collective action potentials of the anatomical structure 50 during a predetermined period of time (e.g., one or more cardiac cycles) may be detected by a device, such as an ECG monitor. The device typically uses electrodes that are placed on the surface of a body or on or within the anatomical structure at predetermined locations to detect the electrical activity (i.e., the action potentials). As shown, the electrical activity of the heart may be represented by PQRST waveforms 64 and 65.

Representative PQRST waveforms 64 and 65 are shown in FIG. 1 and each includes a P wave, a QRS complex, and a T wave. The P wave is caused by the action potentials generated when the atria of the heart depolarize before atrial contraction occurs. The QRS complex is caused by the action potentials generated when the ventricles depolarize before their contraction. As the contraction and pumping action of the heart occurs, repolarization of the heat muscle commences, slowly at first and then more rapidly. The waveforms 64 and 65 may conclude with the T wave and, in some cases, an additional U wave (not shown).

As shown in FIG. 1, the PQRST waveforms 64 and 65 may include several waveform features. A "waveform feature," as used herein, is a measurable quality or characteristic of a waveform that may be associated with a condition of the anatomical structure. For example, a waveform feature can be a length or interval between two points on the waveform, amplitude of one or more waves or deflections, a slope at a predetermined portion of the waveform, or a ratio between two intervals, amplitudes, and/or slopes. FIG. 1 illustrates some commonly used or analyzed waveform features that include a PR segment or interval, a QRS duration, a ST segment, a ST interval, a QT interval, and an R+R interval. Although not shown, other waveform features of interest include TpTe interval, T wave symmetric, T wave notch, U wave. However, the above list of waveform features is not intended to be exhaustive and many more waveform features exist and may be determined in the future. Furthermore, although the waveform features shown in FIG. 1 are with respect to the PQRST waveform, waveform features may also be measured with respect to other waveforms.

Figure 2:
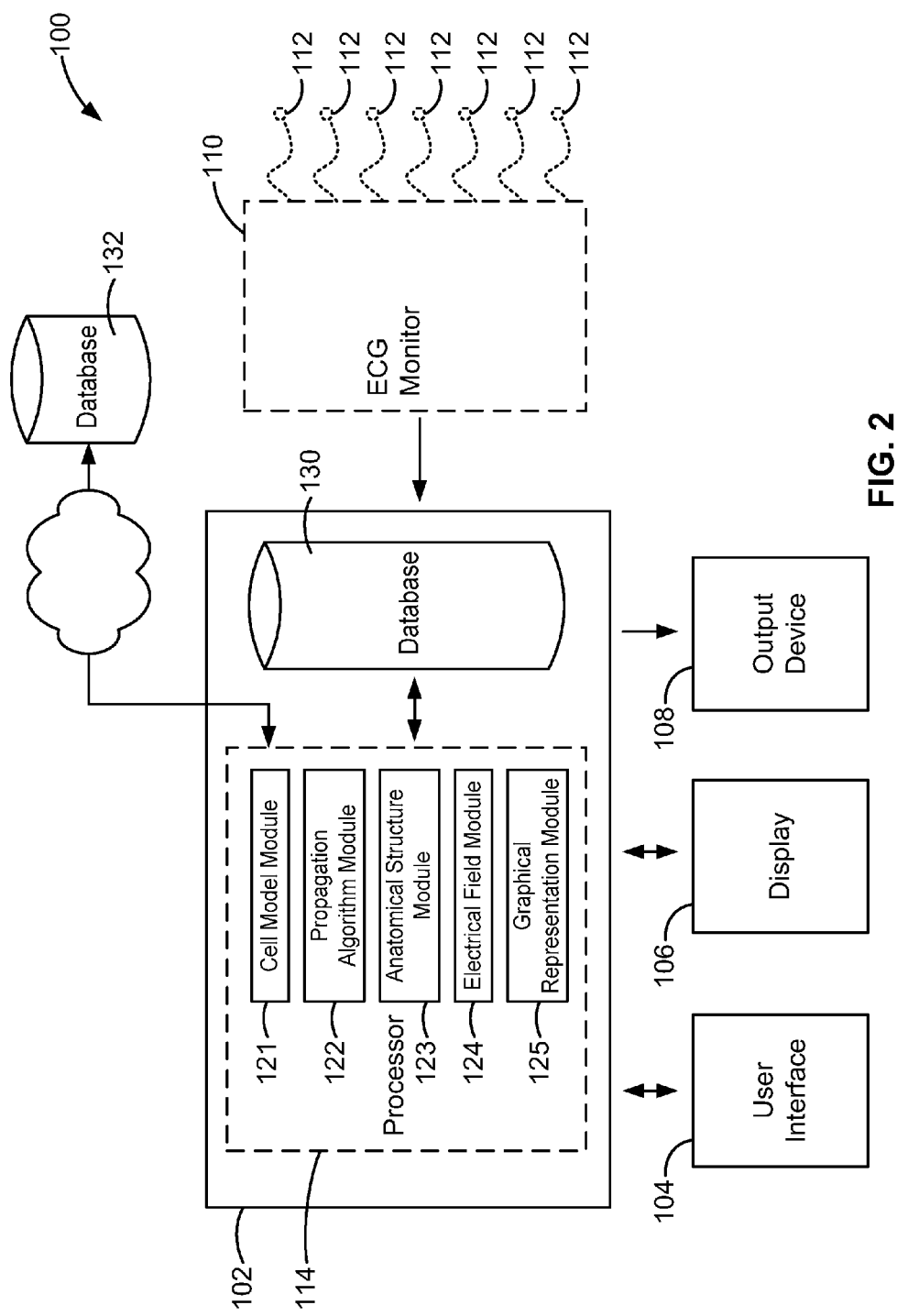
FIG. 2 is a block diagram of an exemplary system for modeling electrical activity of an anatomical structure in accordance with one embodiment.

FIG. 2 is a block diagram of an exemplary system 100 for modeling electrical activity of an anatomical structure and for performing the methods described herein. The system 100 includes a computing device or system 102 that is communicatively coupled to a user interface 104, a display 106, and an output device 108. The system 100 may be integrated into one component (e.g., a laptop computer) or may be several components that may or may not be located near each other. In alternative embodiments, the computing device 102 may be communicatively coupled to an ECG monitor 110 that is, in turn, communicatively coupled to a plurality of electrodes 112 for monitoring an anatomical structure of a patient. The graphical representation of the anatomical structure of the patient may be provided by data from imaging devices like CT or MRI. The electrodes 112 may be placed on a surface of the patient's skin in predetermined locations. The ECG monitor may be configured to receive electrical signals from the electrodes 112. The signals from one electrode may represent a local surface potential detected by the electrode 112.

As used herein, "communicatively coupled" includes devices or components being electrically coupled to each other through, for example, wires or cables and also being wirelessly connected to each other such that one or more of the devices or components of the system 100 may be located remotely from the others. For example, the user interface 104 may be located at one location (e.g., hospital room or research laboratory) and the computing device 102 may be remotely located (e.g., central server system).

The computing device 102 may be, for example, a server system, a workstation, a desktop computer, or a laptop computer. The computing device 102 includes a processor or controller 114 that has or is communicatively coupled to modules for performing methods as described herein. The modules include a cell model module 121, a propagation algorithm module 122, an anatomical structure module 123, an electrical field module 124, and a graphical representation module 125. Each of the modules 121-125 may be communicatively coupled to a memory or database 130 and/or communicatively coupled to a remote memory or database 132 via, for example, the internet. Although the database 130 is shown as being shared by the modules 121-125, each module 121-125 may have a separate memory or database. Furthermore, there may be several additional modules of the processor 114 that are not shown. For example, the processor 114 may include a signal processing module configured to interpret ECG data received from the ECG monitor 110 and other modules used by a user to analyze and interpret data obtained by the system 100.

The databases 130 and 132 may store data that can be retrieved by the components or modules of the system 100 and other remotely located systems through the internet or a local communication network. The databases 130 and 132 may store data that the modules 121-125 may require in order to accomplish the functions of the modules 121-125. For example, the databases 130 and 132 may store data relating to several different kinds of cell or tissue models of electrical activity for specific anatomical structures. The databases 130 may also store patient specific geometry data scanned from imaging devices like CT or MRI. More specifically, the databases 130 and 132 may store cell set data. Cell set data may represent one or more groups of cells (also called cell sets) that interact with each other. For example, one cell within a group may stimulate an adjacent cell within the group, which, in turn, may stimulate another cell within the group. The cells within a group are located within a predetermined spatial location or region of the anatomical structure. Each group of cells may collectively generate or exhibit electrical activity that is detected by one or more electrodes.

Cell set data may include cell models that represent the electrical activity exhibited by groups of cells. By using cell set data, the system 100 may reduce an amount of computation required to model the electrical activity of the anatomical structure. More specifically, a cell model may represent the total electrical activity exhibited by all of the cells within a corresponding group during a predetermined period of time. For example, the cell model may represent electrical activity exhibited by several cardiac cells within the left ventricle during one or multiple cardiac cycles. The cell model may include one or more model parameters in which the electrical activity of the corresponding group of cells is at least partially based upon. Furthermore, cell models may be reconfigurable (e.g., the user may be able to change or somehow affect one or more model parameters that the electrical activity is at least partially based upon). For example, one model parameter may represent a function of ion channels within the group of cells and a user may be able to change the model parameter.

Furthermore, cell set data may include other information regarding groups of cells. For example, the cell set data may include data relating to conduction of a group of cells, geometric or spatial location of a group of cells with respect to other groups of cells or other identifiable features of the anatomical structure. Furthermore, the cell set data may be categorized in other ways. For example, the cell set data may be related to transmural heterogeneity, which focuses on differences among different heart layers, longitudinal heterogeneity, which focuses on differences from a heart base to an apex, and the cell set data may be related to a general scaling factor for each ion channel conductivity.

The databases 130 and 132 may also store propagation algorithms that represent conduction of the electrical activity through the anatomical structure. The propagation algorithms may represent conduction through one cell, a group of cells, or structure (e.g., tissue, layer) within the heart, and the like. The databases 130 and/or 132 may also store two- or three-dimensional renderings or graphical representations of anatomical structures (e.g., muscles, nerves, heart, including specific muscles, structures, and nerves in the heart) that may be displayed on the display 106. The graphical representations may also include or represent windows, graphs, markers, spreadsheets, and the like. In addition, the databases 130 and 132 may store ECG data, image data, patient histories, data mining results, and clinical results from drug trials.

The user interface 104 is configured to accept or receive user inputs from a user of the system 100. The user interface 104 may include at least one of a keyboard, a movable pointing device (e.g., mouse), a voice-activation system, and a touch-sensitive screen. The display 106 may also be the user interface 104. Furthermore, the output device 108 may be a printer, a removable storage device, the display 106 and/or the databases 130 and 132. Output generated by the processor 114 may be formed into graphical representations that are displayed on the display 106 or stored into a storage device. For example, the output may be ECG data displayed on the display 106 or stored in spreadsheets or another format.

In some embodiments, the system 100 is based at least partially on systems described in Xue et al., "Study of Repolarization Heterogeneity and Electrocardiographic Morphology with a Modeling Approach," Journal of Electrocardiology, 41 (2008) 581-587, and in U.S. Patent Application Publication No. 2008/0177192 to Chen et al., which are both incorporated by reference in their entirety. For instance, the cell model module 121 may use any cell or tissue models for determining electrical activity of cells or tissues within the anatomical structure. For example, the cell model module 121 may calculate twelve ion channel currents and generate transmural and longitudinal heterogeneities. The ion channels may include fast and slow potassium channels Ikr, Iks, Ikl, and Ito. Furthermore, the cell model module 121 may use ion current block factors that are either entered by a user or incorporated into the cell model. Ion current block factors may represent a percentage of ion channels that are blocked (e.g., by a chemical or drug).

The propagation algorithm module 122 determines the propagation of electrical impulses throughout the anatomical structure and may work in conjunction with the cell model module 121. For example, an action potential from one cardiac cell may cause an electrical impulse that travels through the cardiac cell and activates action potentials in adjacent cardiac cells. Accordingly, propagation algorithms may be based upon different characteristics of tissues, structures, muscles, and nerves within the anatomical structure. For example, the propagation algorithm module 122 may be based upon factors such as (a) a location of the bundle branch joint point; (b) the Purkinje sheet distribution; (c) propagation speed along the Purkinje sheet, the bundle branch, within cardiac cells; (d) myocardium fiber orientation; (e) and MI-induced propagation change. The above list of factors is not intended to be exhaustive and other factors may be considered.

The electrical field module 124 may use data or information determined by the propagation algorithm and cell model modules 121 and 122 and calculate a surface potential that is ultimately detected by electrodes. The modeled surface potential may represent surface potential detected on a surface of the anatomical structure or on a body of a patient (e.g., the torso). In some embodiments, the system 100 uses a combination of Finite Element Method (FEM) and Boundary Element Method (BEM) to determine the electrical field on any location of the heart and body including torso. As such, the electrical field module 124 may include a bidomain model-based FEM-BEM coupling formulation in the electric field. The electrical field module 124 may consider a three-dimensional geometry and orientation of the anatomical structure with respect to a surface of a torso. More specifically, in one embodiment, a formula for determining the electrical field may be divided into two separate parts: (a) inside the heart and (b) from the heart surface to a torso of the patient. With respect to the part inside the myocardium, an FEM method may be used that considers anisotropy of myocardium. For the second part, a BEM method may be used to calculate potential between the heart and the body surface in order to obtain higher computational efficiency.

Figure 3:
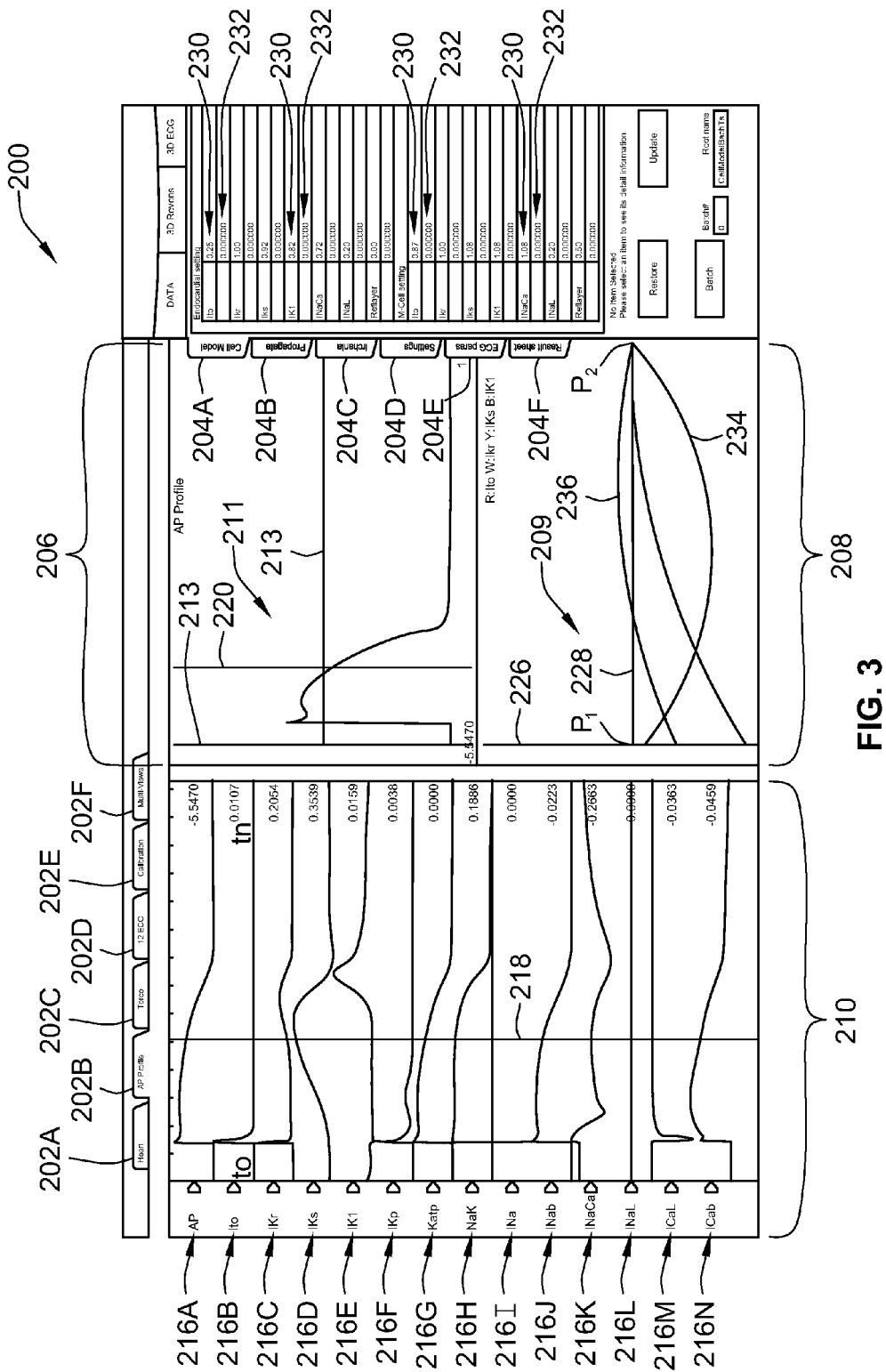
FIG. 3 illustrates a window in accordance with one embodiment that shows electrical activity information of the anatomical structure.

FIG. 3 illustrates a window 200 formed in accordance with one embodiment that may be displayed on the display 106 (FIG. 2). The graphical representation module 125 (FIG. 2) may use data stored within the databases 130 and 132 (FIG. 2) and/or data provided by the modules 121-124 (FIG. 2) to provide a user-friendly interface or display that may facilitate analysis of the electrical activity of an anatomical structure. As shown, the window 200 includes a plurality of tabs 202A-202F and 204A-204F and a plurality of frames 206, 208, and 210 that are viewable in the window 200 when the tab 202B is selected. The window 200 may provide a user-friendly interface that enables the user to interact with the cell modeling used by the system 100 (FIG. 2).

The tab 204A is labeled as a "Cell Model" tab and may enable a user of the system 100 to select, change, or alter each ion channel conductivity setting of the cell models used in modeling the electrical activity of the anatomical structure. For example, the tab 204A lists several settings or factors 230 for ion currents that are typically associated with the action potential of cardiac cells. The settings 230 may relate to model parameters for a corresponding cell model. The tab 204A enables a user to select the type of cell (e.g., endocardial cell, M-cell, and epicardial cell) and enter a user input within each setting 230 that relates to the value of the corresponding ion current. In the illustrated embodiment, the user input may relate to an ion blockage factor that may represent a percentage of conductivity of ion channels that are blocked within the modeled cardiac cells. As an example, the 0.25 entered with respect to the ion current Ito shown in FIG. 3 indicates that 25% of the ion current Ito of the endocardial will be blocked when the electrical activity of the anatomical structure is modeled. In addition, the tab 204A also allows a user to enter a delta value 232 that represents the change in the setting 230 through each iteration of a batch job. More specifically, if a batch job runs ten iterations, the setting 230 for the ion blockage factor will be changed by the delta value 232 after each iteration in the batch job. For instance, if the delta value 232 is 0.01 and there are 10 iterations in the batch job, then the setting 230 will be changed by a total value of 0.1 at the end of iterations.

The tab 202B is labeled as the AP Profile tab (also called an electrical activity tab) and includes information or data regarding the electrical activity of an anatomical structure. More specifically, the tab 202B includes frames 206, 208, and 210. The frame 206 shows information regarding an action potential profile of the anatomical structure or a region of interest (ROI) within the anatomical structure. As shown, the information may be displayed in a graph 211 showing a change in membrane potential over time. In particular, the vertical axis 213 may be in millivolts (mV) and the horizontal axis 215 may be in milliseconds (ms).

The frame 210 provides information regarding ion channels within the anatomical structure or ROI. The frame 210 includes a graph 216A that represents the action potential and illustrates the membrane potential over time. Also, the frame 210 illustrates several ion currents that affect the membrane potential of the action potential in corresponding cell or cells. The ion currents include Ito, IKr, IKs, IKl, IKp, IKatp, INaK, INa, INab, INaCa, INaL, ICaL, ICab, at least some of which are discussed in the above cited U.S. Application Publications or the articles that have been incorporated by reference. Some are also described in Katz, *Physiology of the Heart*, 4$^{th}$ *Edition*, (2006). Each ion current is represented by a graph 216B-216N. With respect to the graphs 216B-216N of the ion currents, a horizontal axis shows time in milliseconds (ms) and a vertical axis shows a value of the current of the corresponding ion current.

As shown in frame 210, the graphs 216A-216N are aligned with each to facilitate determining a current state or value of each ion current with respect to the other ion currents or the action potential at user-selected times. For example, each graph 216 of a corresponding ion current may illustrate a point $t_0$ (only one point $t_0$ is shown), which indicates a time when measurement of the corresponding ion current begins, and a point $t_N$ (only one point $t_N$ is shown), which illustrates a time when measurement of the corresponding ion current ends. Point $t_0$ for each ion current may be vertically aligned with the other points $t_0$ and the point $t_N$ for each ion current may be vertically aligned with the other points $t_N$.

Also shown, a tracking line 218 may extend through the graphs 216A-216N in a vertical direction along the y-axes. The tracking line 218 also facilitates determining a current state or value of each ion current with respect to the other ion currents at a user-selected time. The tracking line 218 may be moved side-to-side along the horizontal axes of the graphs 216. Furthermore, the alignment of the graphs 216 and the tracking line 218 may also facilitate determining a current state or value of each ion current with respect to the action potential graph 216A. For example, the position of the tracking line 218 as shown in FIG. 3 illustrates that during the repolarization stage of the action potential at t=176 ms, the ion current IKs is above a baseline value and the ion current IKl is substantially at a baseline value.

The tracking line 218 may also follow a tracking line 220 shown in the frame 206. The tracking line 220 may be moved side-to-side by the user along the horizontal axis within the frame 206 to a user-selected time (e.g., t=176 ms as shown in FIG. 3). Likewise, the tracking line 218 may be synchronized with the tracking line 220 such that the tracking line 218 is simultaneously moved to the user-selected time.

The frame 208 may provide information regarding transmural dispersion or heterogeneity of a predetermined section of the anatomical structure. As shown, the frame 208 provides a graph 209 having a vertical or y-axis 226 and a horizontal or x-axis 228. The x-axis 228 indicates a position within the anatomical structure between two points P1 and P2. For example, P1 may be a surface of the endocardium within a heart and P2 may be an outer surface of the heart or surface of the epicardium. The y-axis 226 indicates a conductivity (or, alternatively, a resistivity) of certain ion currents. For example, the curve 234 may represent the change in conductivity (i.e., the transmural dispersion or heterogeneity) of the ion current IKs as the heart moves from cardiac cells within the endocardium to cardiac cells within the midmyocardium and to cardiac cells within the epicardium. The curve 236 may represent the change in conductivity of the ion current INaCa. If the ion channels corresponding to the ion currents shown in the frame 208 are blocked by a chemical or drug, a shape of the curves may change. For example, if the ion channels are blocked the corresponding conductivity values would reduce.

Accordingly, the window 200 provides a user-friendly interface that provides quantitative and visual information for analyzing the electrical activity of the anatomical structure. By way of example, a user may desire to understand the effects that a drug or chemical may have on the electrical activity of an anatomical structure. If the user is aware which ion channel(s) may be affected by the drug or chemical and to what extent, the user may enter values into the settings 230 in the tab 204A. After entering such information, the window 200 may be updated to provide quantitative and visual information regarding the action potential and the ion currents that correspond to the action potential. The user may use the tracking lines 218 and 220 to determine which ion currents affect the action potential at different times. Furthermore, the frame 208 may quantitatively and visually show the transmural dispersion of ion currents from two positions in the anatomical structure.

If the user desires, the user may also enter user inputs relating to the delta values 232. The user may then select a number of iterations to run through a batch job. After running the batch job, the system 100 may provide an output (e.g., a spreadsheet displayed on the display 106 or stored in a database or removable device). The output may include data regarding the waveforms obtained through the batch job and values of waveform features.

Figure 4:
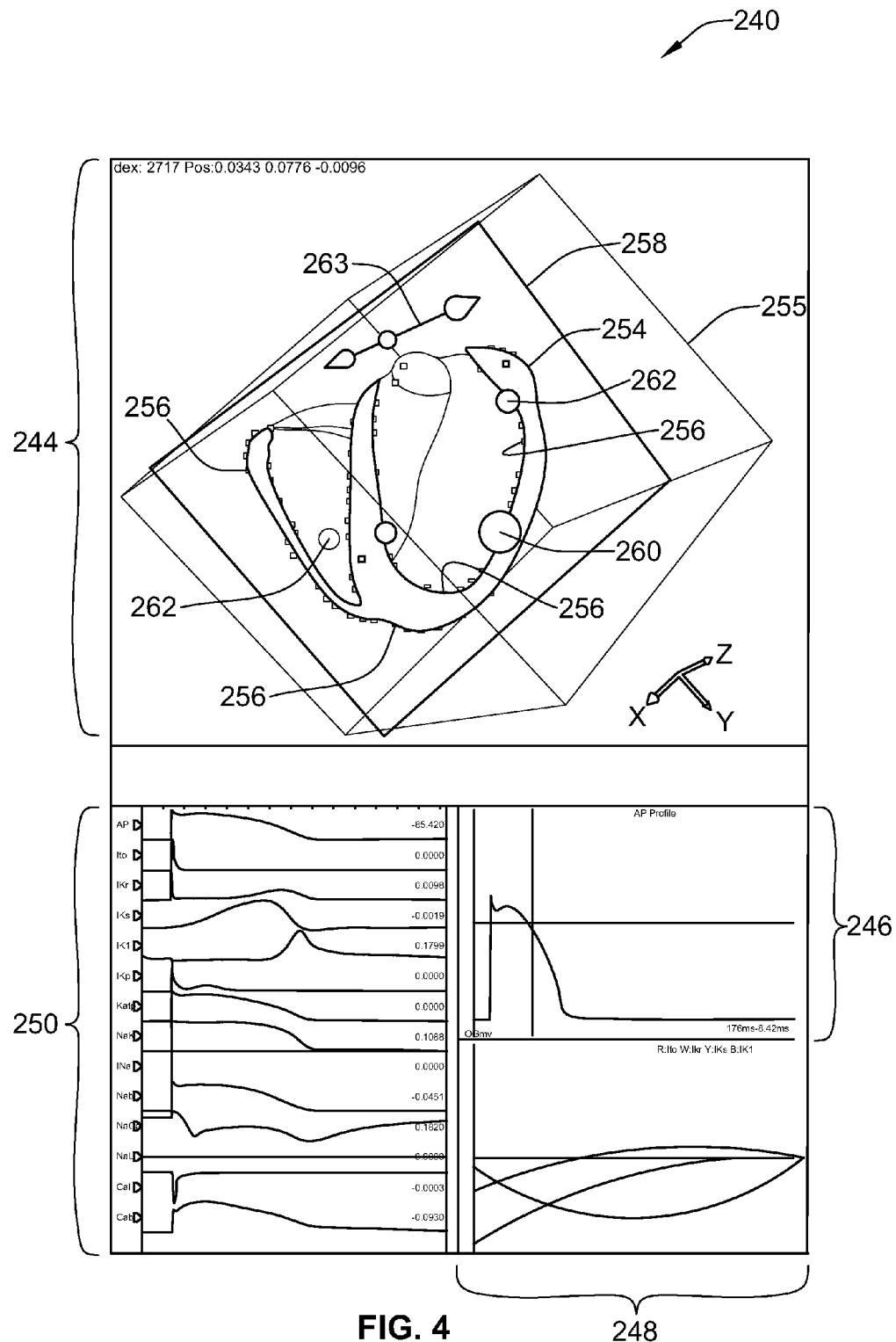
FIG. 4 illustrates a window in accordance with one embodiment that shows electrical activity information in addition to geometric information of the anatomical structure.

FIG. 4 shows a window 240 that includes frames 244, 246, 248, and 250. The frames 246, 248, and 250 may be similar to the frames 206, 208, and 210 described above with reference to FIG. 3. Embodiments described herein may provide an interface that enables a user to select a region-of-interest (ROI) within an anatomical structure and then provide quantitative and visual information regarding the electrical activity of the user-selected ROI. For example, the frame 244 shows a graphical representation 254 of an anatomical structure. The anatomical structure may be a heart as shown in FIG. 4 or may be another anatomical structure, such as a muscle or nerve. The system 100 (FIG. 1) may enable a user to move or change an orientation of the graphical representation 254 to provide a better view for the user. For example, the frame 244 shows axes X, Y, and Z. The anatomical structure may be rotated about any of the axes X, Y, and Z and may also be shifted side-to-side or up-down within the frame 244.

The graphical representation 254 may be provided by the anatomical structure and/or graphical representation modules 123 and 125 (FIG. 2) and retrieved from the database 130 or 132 (FIG. 2). The graphical representation 254 may be a derived from medical images, such as medical images taken from CT or MRI medical imaging. Also, the graphical representation 254 may represent a particular patient's anatomical structure or may be derived from several anatomical structure renderings. For example, the graphical representation 254 may be derived through a plurality of medical images of hearts having a common structural deficiency or anomaly. The graphical representation 254 may also be derived from a plurality of medical images of hearts that are determined to have a particular cardiac condition or to be in a healthy condition.

As shown in FIG. 4, the graphical representation 254 is within a three-dimensional box or enclosure 255. The enclosure 255 may facilitate a user in understanding the orientation of the anatomical structure. Also shown, the graphical representation 254 is a cross-section of the anatomical structure (e.g., a cross-section of the heart). A cross-sectional plane 258 is also shown that indicates where the cross-section of the heart is taken. The plane 258 may be movable through the graphical representation 254 of the heart (and the enclosure 255) if the user desires to change the view. As shown in FIG. 4, the plane 258 substantially faces the user that is viewing the window 240. However, the plane 258 and the enclosure 255 may also be moved (i.e., re-oriented) about the X, Y, and Z axes simultaneously with the graphical representation 254 or independent from the graphical representation 254 so that the user may choose different cross-sectional views. Furthermore, the frame 244 may also provide an arrow 263 to assist the user in understanding the orientation of the anatomical structure.

Furthermore, the graphical representation 254 may include a plurality of cell markers 256. Each cell marker 256 represents a group of cells located in the indicated region of the anatomical structure. As discussed above, cell set data may include a cell model that represents the electrical activity of the group of cells corresponding to the cell marker 256. The number of cell markers 256 shown may be indicative of the number cell models that will be computed to determine the electrical activity of the anatomical structure. Accordingly, as the density of cell markers 256 increases, the number of computations performed by the system 100 increases. In some embodiments, the user of the system 100 may select the density of cell markers 256.

The user interface 104 (FIG. 2) may be configured to accept user inputs for selecting the ROI. The ROI may designate a particular location or spatial region within the anatomical structure that is represented by the graphical representation 254. For example, the graphical representation module 125 may provide a probe marker 260, which is shown as a spherical and slightly transparent image in FIG. 4. The system 100 may enable the user to move the probe marker 260 to a desired location or spatial region within the graphical representation 254 of the anatomical structure. In FIG. 4, the probe marker 260 is located along a surface of a ventricle of the heart.

In the illustrated embodiment, a volume or space of the anatomical structure that is covered by the probe marker 260 indicates the ROI to be modeled. As shown, the probe marker 260 may enclose or cover cell markers 256. When the system 100 computes the electrical activity of the anatomical structure, the system 100 may only use the cell models that correspond to the cell markers 256 that are within the ROI. As such, the electrical activity of the ROI may be determined. By way of an example, after the user locates the probe marker 260 on the graphical representation 254, the system 100 may then use the cell models that correspond to the cell markers 256 within the ROI to determine the electrical activity of the ROI. The processor 114 may take an average of each ion current, action potential, transmural dispersion curve, or any other computable measurement from each cell model within the ROI. These averages may then be displayed, for example, in frames 246, 248, and 250. In an alternative embodiment, the processor 114 may only use the cell model of the cell marker closest to a center point of the probe marker 260.

By enabling a user to view a cross-section of the anatomical structure, a user may view and analyze groups of cells not viewable from a surface of the anatomical structure. For example, the user may select an ROI that includes cell markers 256 within a wall or another tissue layer of a heart. The probe marker 260 may include or cover multiple tissue layers (e.g., from the endocardium to the epicardium).

In addition to being movable, the probe marker 260 may also be adjustable in size and shape to change the ROI. As one example, the user may be able to select the probe marker 260 and adjust a diameter of the spherically shaped image so that the probe marker 260 may cover more cell markers 256. Furthermore, other shapes for the probe marker 160 may be used to cover different cell markers 256. Also, in alternative embodiments, the user of the system 100 may directly select predetermined structures, layers of cells, or individual cell markers 256 to determine the ROI that is to be modeled.

Furthermore, a user may also select and locate blockers 262, for example, on the conduction pathway of Purkinje Sheet (PK Sheet). The blockers 262 may represent portions of the heart where electrical conduction through the blocker is "blocked." For example, in some cardiac conditions, the conductive pathway to the left side of the heart can be blocked, then a left Bundle Branch Block (LBBB) is formed. Likewise, if the pathway on the PK sheet to the right side of the heart is blocked, then a Right Bundle Branch Block (RBBB) is formed. As shown, the blockers 262 may be located in spatial regions that are electrically connected with the region of the anatomical structure designated by the probe marker 260. Accordingly, the blockers 262 provide an additional tool for modeling the electrical propagation activity of the anatomical structure.

Figure 5:
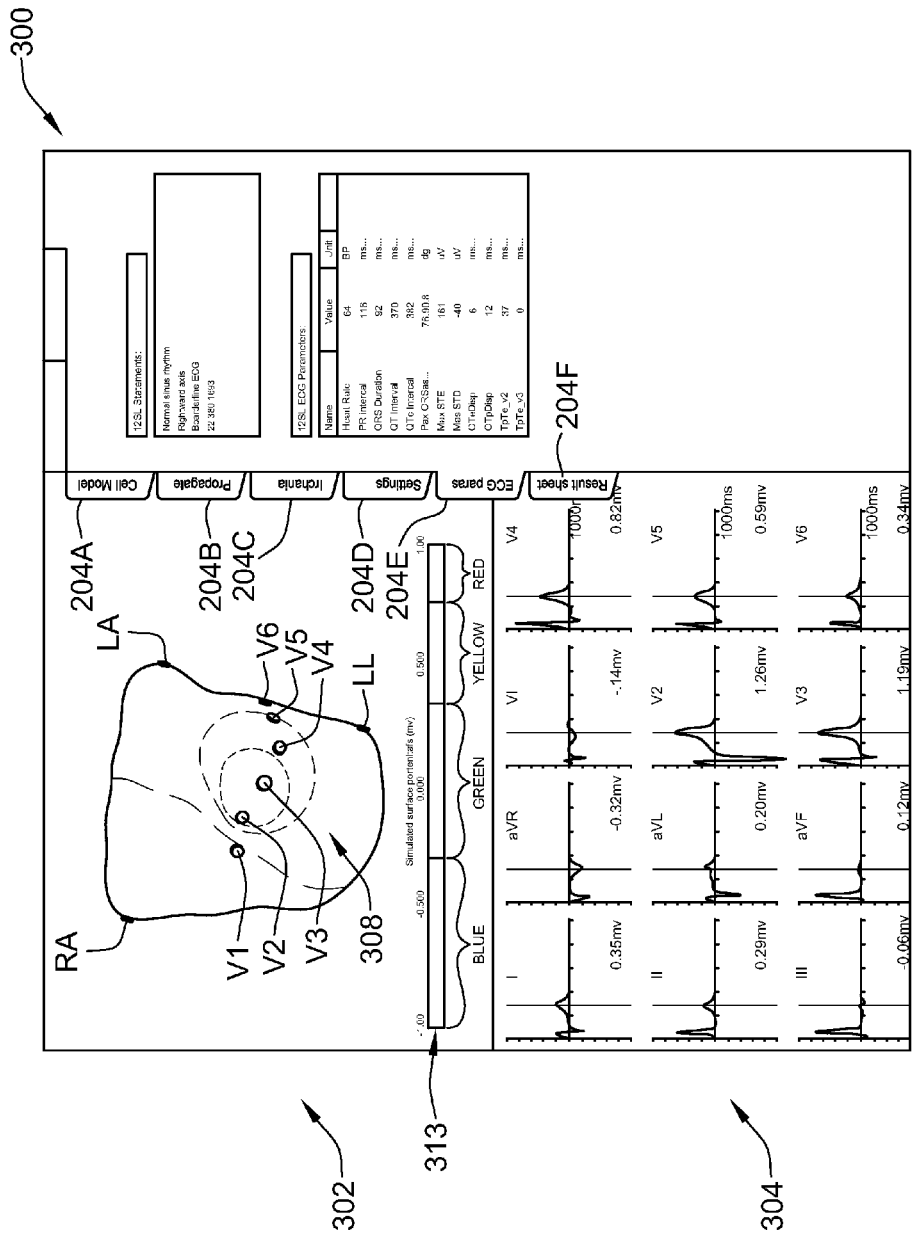
FIG. 5 illustrates a window in accordance with one embodiment that shows body surface potential map (BSPM) with respect to electrode locations.

FIG. 5 shows a window 300 that includes frames 302 and 304 and the tabs 204A-204F. The tab 204E is selected in FIG. 5 and shows the values of predetermined waveform features, which may also be called ECG parameters. The waveform features correspond to a modeled body surface potential map (BSPM) of a torso of a human body. In some instances, ECG and BSPM represent the same information or readings. However, ECG data, by its name, is only directed toward data that correlates to electrical activity of the heart. BSPM data may be correlated to more information of electrical activity of the heart or another anatomical structure. Standard ECG is a subset of BSPM. In most cases, ECG represents major electrical activity of the heart, but on other cases, ECG might miss some specific electrical activity of the heart.

The frame 302 shows a graphical representation 306 of a torso having a plurality of electrodes 308 located at predetermined locations. In some embodiments, the system 100 (FIG. 2) may indicate the BSPM along the torso. For example, the system 100 may indicate the BSPM through a color-coding as indicated in a chart or legend 313. Red and yellow may represent a positive potential and blue may represent a negative potential. Green may represent a potential that is close to zero and may be slightly positive or slightly negative. However, FIG. 5 only shows the BSP of the torso at one particular time. Throughout a cardiac cycle, the BSP at various points on the surface of the torso may change. As such, the distribution of color in a map along the torso surface may change with the cardiac cycle. By way of example, the user may view the BSP of the torso during one or more cardiac cycles and watch the BSP change (i.e., watch the color density or distribution change) as if watching a movie of the cardiac cycles. Furthermore, the user may view the BSP of the torso at individual user-selected times or frame-by-frame. As such, the processor may be configured to present a "movie mode" of the BSP as well as other functional maps (discussed below).

The arrangement of electrodes 308 shown in FIG. 5 is a conventional arrangement for obtaining ECG data where the ten electrodes are positioned to form twelve leads. The waveforms recorded by the ten electrodes in FIG. 5 may be similar to the PQRST waveform described above with respect to FIG. 1. Specifically, the electrodes 308 include a right arm electrode RA; a left arm electrode LA; chest electrodes V1, V2, V3, V4, V5 and V6; a right leg electrode RL (not shown in the frame 302); and a left electrode leg LL. The frame 304 includes graphs illustrating readings from the conventional twelve ECG leads. The twelve ECG leads include leads I, II, V1, V2, V3, V4, V5 and V6 which can be either acquired directly from the patient signals or from model simulated electrical signals, and leads III, aVR, aVL and aVF which are derived using Einthoven's law. The graphs shown in the frame 304 collectively form the conventional PQRST waveform that is may be read by researchers and health practitioners.

When ECG data is recorded from a patient, the twelve ECG leads produce twelve different waveforms or signals that represent the electrical activity of the patient's heart with varying degrees of precision. The precision of a reading for a particular lead is based, in part, on the placement of the corresponding electrode or electrodes. The electrodes V1, V2, V3, V4, V5, V6, RA, LA, RL, LL that are in closest proximity to and/or are most optimally aligned with the electrical activity of the heart at any given time receive the strongest signal and are therefore best adapted to monitor such electrical activity. As shown in the frame 302, the electrodes 308 are located in their respective optimal or desired locations.

In accordance with some embodiments, the cell-to-ECG forward modeling performed by the system 100 (FIG. 2) may facilitate a user in identifying waveform features that are associated with one or more cardiac conditions that may occur naturally or after administering a drug. The identified waveform features may be detected through the conventional arrangement of electrodes as shown in the frame 302 or may be detected through a different arrangement. Likewise, the cell-to-ECG forward modeling performed by the system 100 may facilitate a user in determining an optimal position of the electrodes for detecting the identified waveform features. The determined optimal number and position of electrodes for detecting the cardiac conditions may be in the conventional arrangement as shown in the frame 302, or the optimal number and positions of electrodes may have a different number and arrangement.

Furthermore, although FIG. 5 indicates four separate colors (blue, green, yellow, and red), the color-coding or mapping of the torso and the heart may transition through a spectrum of colors (i.e., many more than four colors). For example, green may smoothly transition into yellow (instead of abruptly changing) as the surface potential increases, and yellow may smoothly transition into red. For example, as shown in FIG. 5, electrodes V2 and V3 are on a surface or in an area of the torso that is substantially red (V3 may be on a redder surface than V2). Electrodes V4 and V5 may be in an area that is substantially yellow. V6 may be in an area that is substantially green. V1 may be in an area that is transitioning from blue to green. However, in alternative embodiments, there may be a limited number of colors where each color covers a range of surface potential. Furthermore, alternative ways of distinguishing surface potential on the torso other than colors may be used.

Figure 6:
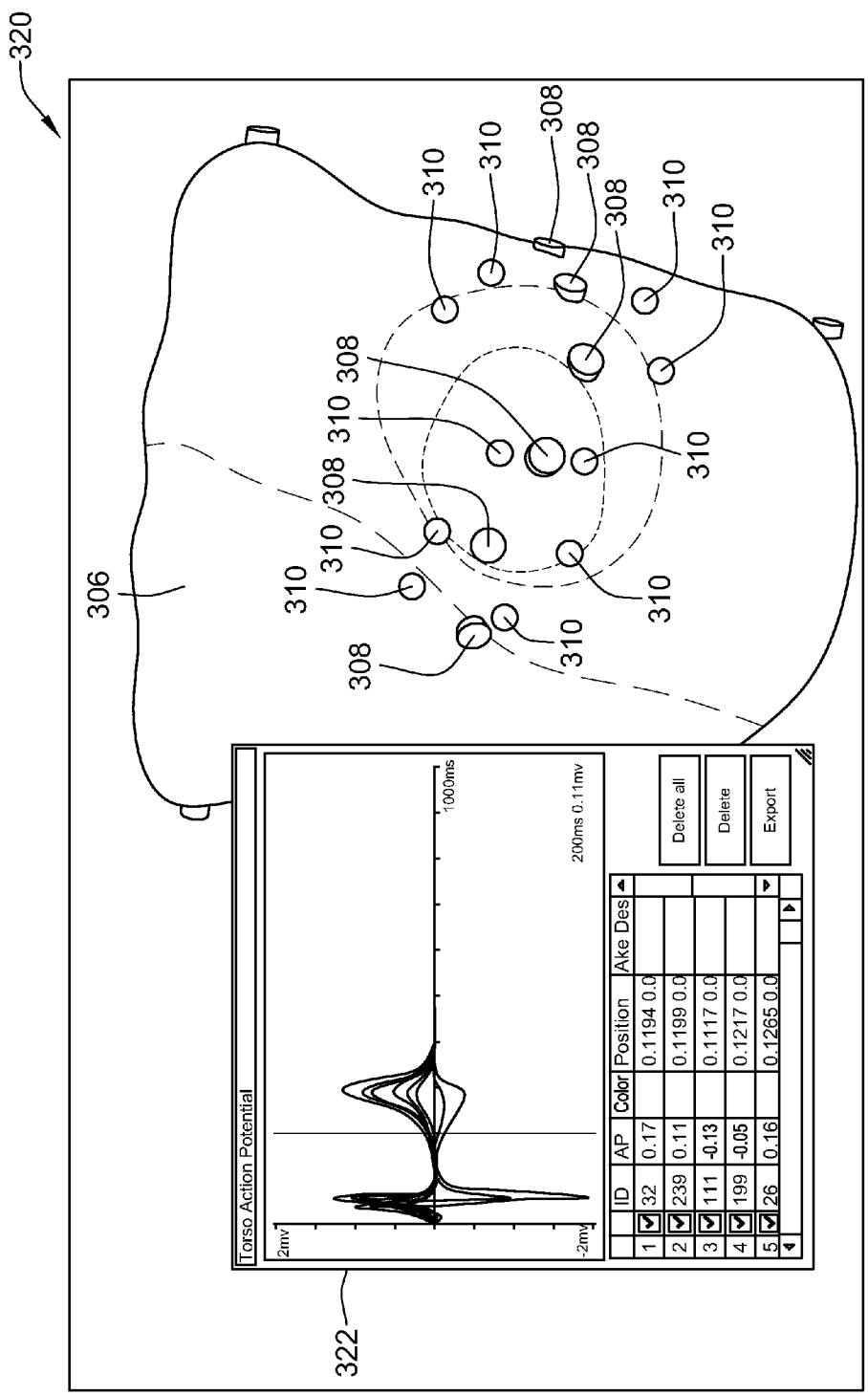
FIG. 6 illustrates a window that shows the BSPM with respect to the electrodes in FIG. 5 and with respect to alternative electrodes.

FIG. 6 shows a window 320 with another window 322 overlaying the window 320. The window 320 includes an enlarged view of the graphical representation 306 of the torso including the conventional arrangement of electrodes 308 as well as additional electrodes 310 positioned at different points along the surface of the torso. The window 322 shows the BSP at points that correspond to the locations of the electrodes 310. Accordingly, a user may select different points (or electrodes 310) along the surface of the torso and view a modeled BSP reading for each point. Also, the user may simultaneously select many points along the surface and view the BSP readings simultaneously in the window 320. The window 322 may facilitate a user identifying new electrode locations or electrode arrangements that may offer better readings to identify certain cardiac conditions. For example, waveforms detected from the new electrode locations or electrode arrangements may have waveform features that have a high correlation to one or more cardiac conditions. In addition to the above, the system 100 (FIG. 2) may also determine and display a bipolar potential between any two points or electrodes 308 or 310.

Although not shown in FIG. 6, the system 100 may also produce a body surface potential map (BSPM). To make or conduct a BSPM, several electrodes (e.g., 96 electrodes) are placed across the torso of the body of a patient or several patients. The ECG data gathered from the one or more patients may be used to develop alternative lead arrangements as well as alternative electrode locations. Similarly, the system 100 may be used to produce a similar BSPM using the cell models. As one example, a researcher investigating the effects of a drug may conduct a BSPM for a heart that is affected by the drug. The drug may block one or more ion channels thereby reducing the ion current within the corresponding cells. The BSPM developed from the forward modeling may facilitate determining electrode locations or lead arrangement that provide waveform features that are highly correlative with cardiac conditions caused by the drug.

Furthermore, the BSPM may facilitate determining electrode arrangements that provide some tolerance in misplacing the electrode. For instance, there are several factors that may result in less than optimal readings. For example, electrodes placed onto a body of a patient may be misplaced by a technician, the body type of the patient may be significantly different than the standard body type, and the heart structure or function may be different from the standard may all reduce the effectiveness of the monitor to detect the electrical activity of the heart. Accordingly, the BSPM may facilitate identifying electrode locations and arrangements that may allow some error in placement of the electrodes and still provide effective and reliable readings of the electrical activity (i.e., readings that may be used to identify waveform features).

Figure 7:
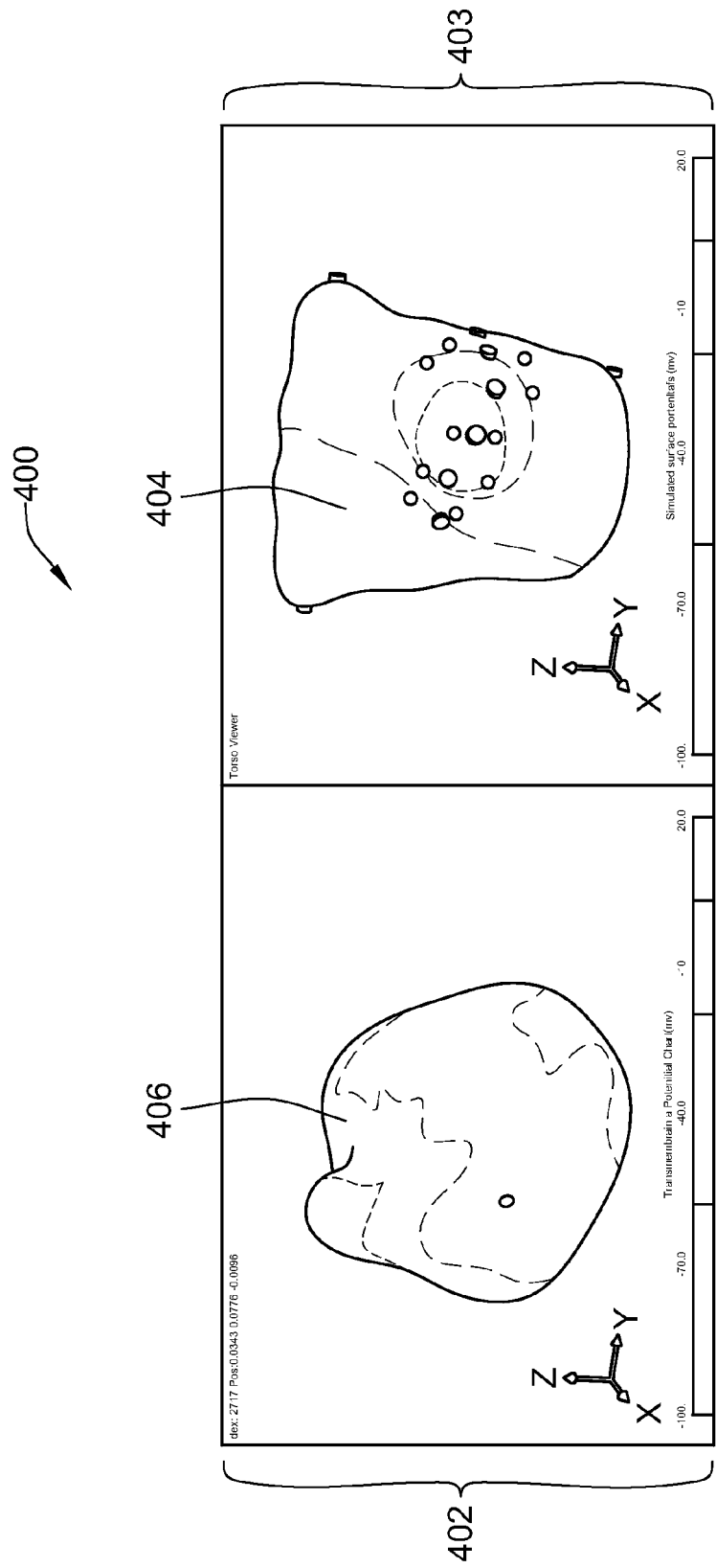
FIG. 7 illustrates a window in accordance with one embodiment that shows the BSPM synchronized with a functional map of the anatomical structure.

FIG. 7 shows a window 400 that includes frames 402 and 403. In some embodiments, the different frames and functions described above may be synchronized with respect to each other and shown within the same window. For example, the frame 403 illustrates a graphical representation 404 of a torso that indicates a BSP distribution of the torso, and the frame 402 illustrates a graphical representation 406 of a heart that indicates a transmembrane potential (TP) of a surface of the heart. The BSP of the torso may be color-coded in the graphical representation 404 and the TP of the heart may be color-coded in the graphical representation 406. The BSP and TP may be synchronized so that the system 100 (FIG. 2) may provide the user with a visual representation of the BSP and TP at user-selected times within a predetermined period of time (e.g., one cardiac cycle). The process of estimating TP from a time series of known BSPM is called an 'Inverse Solution' of the heart. Conversely, estimating the BSPM from the TP is called a 'Forward problem or solution' of the heart. The Cell-to-ECG program may solve, separately or together, the Inverse and Forward problems.

Figure 8:
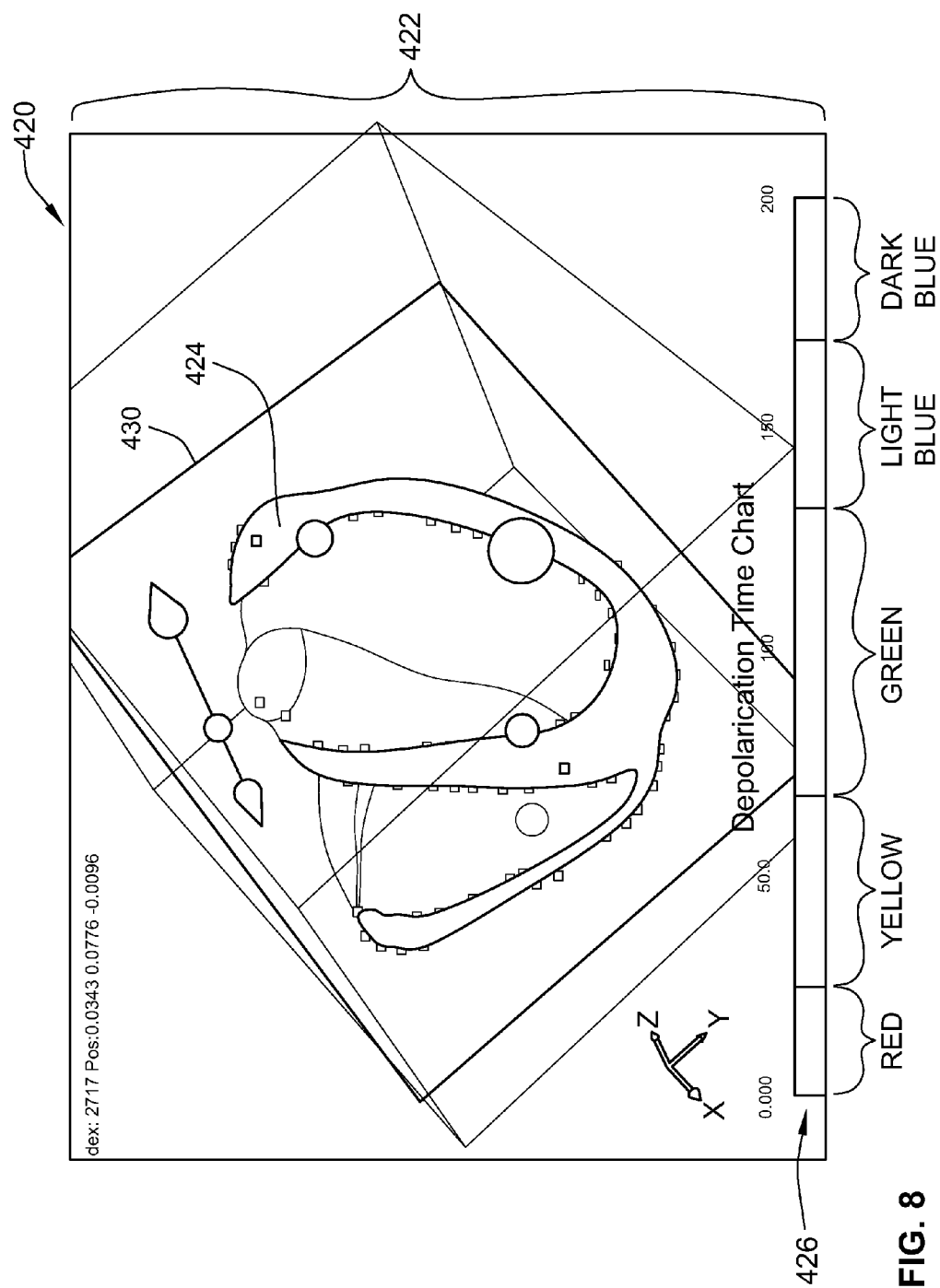
FIG. 8 illustrates a window in accordance with one embodiment that shows a functional map of an action potential (AP) feature on a cross-section of the heart that shows the heart's internal structure.

FIG. 8 shows a window 420 that has a frame 422 illustrating a graphical representation 424 of an anatomical structure. More specifically, the graphical representation 424 is a cross-sectional view of a heart. Embodiments described herein may provide functional maps of anatomical structures. As used herein, a "functional map" is a graphical representation of an anatomical structure that also provides visual information of features relating to the electrical activity of the anatomical structure while the anatomical structure is functioning. Furthermore, the functional map (i.e., the graphical representation 424 illustrating the functional map) may be moved or re-oriented within the frame 422 as discussed above with reference to FIG. 3. Also, a plane 430 may be moved through the graphical representation 424 to view different cross-sections of the anatomical structure.

For example, the graphical representation 424 is a functional map that illustrates a depolarization time chart. The depolarization time chart indicates when regions of the heart depolarize with respect to the other regions. The depolarization time chart may be color-coded. For example, as indicated by a chart or legend 426, regions of the heart that are depolarized within 0 to 25 ms from an initial activation of the SA node may be colored red. Regions of the heart that are depolarized at 40 to 60 ms after the initial activation may be colored yellow. Regions of the heart that are depolarized at 170 to 200 ms after the initial activation may be colored dark blue.

Although not shown, several other functional maps may be provided. Some functional maps, like the depolarization time chart, may be related to action potential (AP) features of each cell within the anatomical structure. An AP feature can be related to the depolarization, repolarization, amplitude, frequency, or duration of an action potential. More specifically, functional maps of AP features may include depolarization maps that show membrane potential of the cells during depolarization (e.g., from 0 to 50 ms or another time frame); repolarization maps that show the membrane potential of the cells during repolarization; amplitude functional maps that show the amplitude of the action potential of each cell; and action potential (AP) duration map. The depolarization map may also be called an isochron map. Another example of a functional map is a frequency map generated by frequency analysis (e.g., using the Fourier Transform or other transforms) from endocardial or epicardial signals. Those signals can be generated either from a model, or from directly sampling from patients, for example, from an electrophysiology laboratory (EP lab). One specific type of frequency map that may be generated by systems herein is called a dominant frequency map.

The functional maps may provide a visual representation of how different cardiac conditions exhibit different electrical activity in the heart to facilitate the user's analysis. Certain functional maps may be time-dependent and viewed in a movie mode, frame-by-frame, or at specific user-selected times. Furthermore, the color-mapping of the functional maps (or the surface potential mapping of the heart) may be similar to the color mapping as described with respect to FIG. 5. For example, the colors may smoothly transition through a spectrum of colors.

FIG. 9 shows a method 500 for modeling electrical activity of an anatomical structure. The method 500 includes providing a computing system at 502 that includes a database that is configured to store cell set data, and specific geometry data of anatomical structure of the heart to be analyzed. The cell set data may represent a group of cells of the anatomical structure. The cell set data may include a cell model that represents electrical activity of the group of cells. The cell model may have a model parameter that relates to ion channels in the cells. The electrical activity represented by the cell model may be at least partially based upon the model parameter. The method 500 also includes accepting user inputs at 504 that change the model parameter. For example, the user inputs may change a value of the model parameter to form a reconfigured cell model. The method 500 also includes displaying the user inputs at 506 and determining the electrical activity of the anatomical structure at 508 using the cell models including the reconfigured cell model. Output relating to the electrical activity may be generated at 510. The output may be in the form of images on a display, graphs, spreadsheets, printouts, or stored data. Furthermore, results from the modeling can be stored in the database and presented on a spreadsheet. The output may be reviewed visually by selecting (e.g., double clicking) any row of the spreadsheet. The rows may contain data on any measurable or computable data, such as a waveform feature.

FIG. 10 shows a method 600 for modeling electrical activity of an anatomical structure. The method 600 includes providing a computing system at 602 that includes a database that is configured to store cell set data that may represent a group of cells of the anatomical structure. The cell set data may include a cell model that represents electrical activity of the group of cells. The method 600 includes displaying a graphical representation of the anatomical structure at 604 and accepting user inputs at 606 for selecting a region-of-interest (ROI) within the anatomical structure that includes the group of cells. The user inputs may be indicated on the graphical representation of the anatomical structure. The method 600 also includes determining the electrical activity of the ROI at 608 based upon the cell model.

Figure 11:
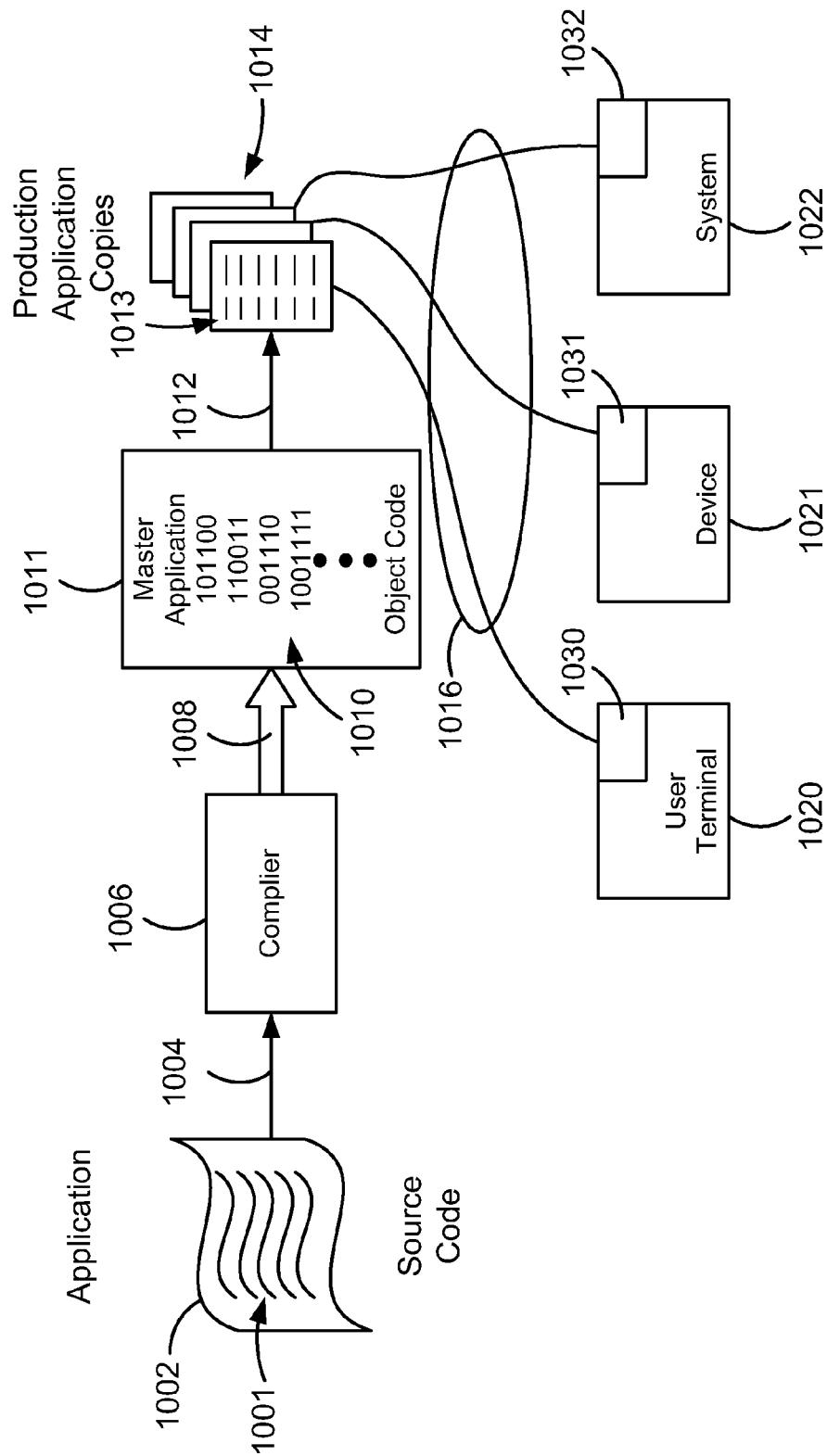
FIG. 11 is a block diagram of exemplary manners in which embodiments of the invention may be stored, distributed, and installed on computer readable medium.

FIG. 11 is a block diagram of exemplary manners in which various embodiments described herein may be stored, distributed, and installed on computer readable medium. In FIG. 11, an "application" represents one or more of the methods and process operations discussed above. As shown in FIG. 11, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous times, as denoted by path 1012, to produce production application copies 1013 that are saved on separate production computer readable medium 1014. The production computer readable medium 1014 is then conveyed, as denoted by path 1016, to various systems, devices, terminals and the like. In the example of FIG. 11, a user terminal 1020, a device 1021 and a system 1022 are shown as examples of hardware components, on which the production computer readable medium 1014 are installed as applications (as denoted by 1030-1032).

The source code may be written as scripts, compiled, or in any high-level or low-level language. Examples of the source, master, and production computer readable medium 1002, 1011 and 1014 include, but are not limited to, CDROM, RAM, ROM, Flash memory, RAID drives, memory on a computing system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011, or 1014 between two geographic locations. The paths 1004, 1008, 1012, and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, inter-continental and the like.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

The various embodiments and/or components, for example, the monitor or display, or components and controllers therein, also may be implemented as part of one or more computers or processors. The computer or processor may include a computing device, an input device, a display unit, and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is complied to run on both 32-bit and 64-bit operating systems. A 32-bit operating system like Windows XP™ can only use up to 3 GB bytes of memory, while a 64-bit operating system like Window's Vista™ can use as many as 16 exabytes (16 billion GB). The Cell-to-ECG program may benefit from using a large memory since the modeling and simulation of a large number cells on the heart would likely be more realistic than using a small number of cells.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

A technical effect of the various embodiments of the systems and methods described herein include user-friendly interfaces for modeling electrical activity of an anatomical structure. Another technical effect includes an interface that provides quantitative and visual information regarding the electrical activity of an anatomical structure. Furthermore, another technical effect includes an interface that facilitates a user selecting a region-of-interest (ROI) within an anatomical structure and that provides visual and quantitative information regarding the electrical activity of the ROI. In some embodiments, another technical effect includes providing a system and method for determining a number and arrangement of electrodes on a surface of a patient to analyze waveform features. Other technical effects may be provided by the embodiments described herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for using a computing system to identify a cardiac condition in a patient associated with changes in electrical activity of an ion channel containing cardiac cells of an anatomical structure by identifying multiple waveform features associated with cardiac conditions in response to a simulated application of a drug or chemical, the method comprising:
   using an electrocardiographic monitor to detect electrical activity of an anatomical structure of the patient;
   storing, in a database:
      the detected electrical activity of the anatomical structure of the patient;
      a propagation algorithm representing conduction of the electrical activity through the anatomical structure; and
      cell set data corresponding to a group of ion channel containing cardiac cells, wherein the cell set data includes a plurality of cell models, each cell model including a waveform representing electrical activity exhibited by at least one of the cells in the group of ion channel containing cardiac cells during a predetermined period of time, wherein the electrical activity represents a functioning of the ion channels in the at least one cell; and
   using a processor of the computing system to:
      accept user inputs from a user interface, the user inputs including selection of a simulated drug or chemical parameter;
      apply the simulated drug or chemical parameter to a cell model from the plurality of cell models, wherein the application of the simulated drug or chemical parameter changes an ion channel conductivity and an electrical activity of the cell model;
      form at least one reconfigured cell model representing electrical activity of a modeled anatomical structure resulting from the changes in the ion channel conductivity due to the application of the simulated drug or chemical parameter to the cell model;
      identify waveform features in the electrical activity of the ion channel containing cardiac cells of the modeled anatomical structure based on the at least one reconfigured cell model associated with a cardiac condition;
      calculate a body surface potential map on the body of the patient using the propagation algorithm and the identified waveform features; and
      use the body surface potential map to select alternate electrode locations for recording the electrical activity of the ion channel.

2. The method of claim 1 wherein the simulated drug or chemical parameter includes a blockage factor for the ion channels and the user inputs designate the blockage factor.

3. The method of claim 1 wherein the simulated drug or chemical parameter is a plurality of simulated drug or chemical parameters, each simulated drug or chemical parameter relating to corresponding ion channels that affect the electrical activity represented by at least one cell model wherein the user inputs relate to at least one of the simulated drug or chemical parameters.

4. The method of claim 1 wherein the cell model includes a plurality of cell models having the simulated drug or chemical parameter, wherein the user inputs relating to the simulated drug or chemical parameter change the electrical activity represented by the plurality of cell models.

5. The method of claim 1 wherein the anatomical structure of the patient is a heart.

6. The method of claim 1 wherein the anatomical structure of the patient is a region or layer of cardiac cells.

7. The method of claim 1 wherein the processor is configured to generate an output representative of the electrical activity of the anatomical structure of the patient, the output providing at least one of a waveform of the electrical activity and values relating to waveform features.

8. The method of claim 7 wherein the output represents the electrical activity as being detected on a surface of a body of the patient.

9. The method of claim 1 wherein the processor is configured to generate a functional map of the anatomical structure of the patient, the functional map being displayed on the display and relating to an action potential (AP).

10. The method of claim 9 wherein the functional map includes a cross-sectional view of the anatomical structure of the patient.

11. The method of claim 9 wherein the functional map indicates a change in the AP feature over a predetermined period of time.

12. The method of claim 11 wherein the change in the AP feature is displayed in a movie mode.

13. The method of claim 1 wherein the user interface is configured to accept user inputs relating to a delta value and a number of iterations, wherein the processor is configured to determine the electrical activity of the modeled anatomical structure for the number of iterations and wherein a difference between the model parameters used during subsequent iterations is the delta value.

14. A method for identifying a cardiac condition of a patient by comparing changes in electrical activity of cardiac behavior of the patient to cardiac behavior due to a simulated application of drugs or chemicals, the method comprising:
    using an electrocardiographic monitor to detect electrical activity of the patient's heart;
    using a computing system that includes a database to:
        store the detected electrical activity of the patient's heart, a propagation algorithm representing conduction of the electrical activity through the anatomical structure, and cell set data corresponding to a group of cells of the heart, the cell set data including a plurality of cell models, each cell model representing electrical activity exhibited by at least one of the cells in a group of ion channel containing cardiac cells during a predetermined period of time, wherein the electrical activity represents a functioning of ion channels in the at least one cell;
        accept one or more user inputs from a user interface of the computing system, the one or more user inputs selecting a simulated drug or chemical parameter, wherein the computing system is configured to apply the simulated drug or chemical parameter to at least one of the plurality of cell models and change an ion channel conductivity and an electrical activity of the at least one cell model responsive to the simulated drug or chemical parameter;
        form at least one reconfigured cell model from the application of the simulated drug or chemical parameter to the at least one cell model, the at least one reconfigured cell model representing electrical activity of the at least one cell model due to the application of the simulated drug or chemical parameter;
        identify a waveform pattern in at least one reconfigured cell model associated with a cardiac condition represented by the at least one reconfigured cell model;
        calculate a body surface potential map on the body of the patient using the propagation algorithm and the identified waveform features; and
        use the body surface potential map to select alternate electrode locations for recording the electrical activity of the ion channel.

15. The method of claim 14 wherein the simulated drug or chemical parameter includes a blockage factor for the ion channels and the user inputs designate the blockage factor.

* * * * *